United States Patent [19]

Kula et al.

[11] Patent Number: 5,238,838
[45] Date of Patent: Aug. 24, 1993

[54] L-CARNITINE AMIDASE PRODUCED BY A MICROORGANISM

[75] Inventors: Maria-Regina Kula, Niederziehr/Hambach; Ulrich Joeres, Mönchengladbach, both of Fed. Rep. of Germany

[73] Assignee: Degussa Aktiengesellschaft, Fed. Rep. of Germany

[21] Appl. No.: 835,860

[22] Filed: Feb. 18, 1992

[30] Foreign Application Priority Data

Feb. 28, 1991 [DE] Fed. Rep. of Germany ....... 4106375

[51] Int. Cl.$^5$ .......................... C12N 9/80; C12N 9/14; C12P 13/00
[52] U.S. Cl. ..................... 435/228; 435/128; 435/195
[58] Field of Search .................. 435/228, 128, 195

[56] References Cited

U.S. PATENT DOCUMENTS 4,918,012 4/1990 Nakayama et al. ................. 435/128

FOREIGN PATENT DOCUMENTS 0158194 10/1985 European Pat. Off. ......... 435/252.1
8504900 11/1985 European Pat. Off. ......... 435/252.1

OTHER PUBLICATIONS

Japanese Patent Abstracts JP1222796 Sep. 6, 1989.
Japanese Patent Abstracts JP1222797 Sep. 6, 1989.

Primary Examiner—David M. Naff
Assistant Examiner—Deborah K. Ware
Attorney, Agent, or Firm—Cushman, Darby & Cushman

[57] ABSTRACT

The microorganism DSM 6230 produces an enzyme, L-carnitine amidase. This microorganism and/or the enzyme which it produces can selectively hydrolyze L-carnitine amide and/or the L-component of DL-carnitine amide to L-carnitine.

1 Claim, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 48 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

Gly Ser Arg Glu Ile Leu Asp Phe Lys Asp Leu Ser Ser Pro Ser Ala
 1               5                  10                  15

Pro Ala Glu Leu Val Ala Asn Ala Ala Phe Leu Glu Pro Ala Gly His
            20                  25                  30

Ala Ala Ala His Glu Pro Phe Asn Gly Gln Ile Thr Leu Gly Glu Thr
        35              40                  45

L-CARNITINE AMIDASE PRODUCED BY A MICROORGANISM

The present invention relates to a new microorganism, a method of obtaining an enzyme from it, the enzyme obtained from it, and the use of that enzyme to produce L-carnitine.

BACKGROUND OF THE INVENTION

L-carnitine (3-hydroxy-4-trimethylaminobutyrate) is the exclusively physiologically active form of carnitine. It is widely known in the animal kingdom and has also been identified in plants. D-carnitine has never been identified in animal tissues. L-carnitine transports long-chain, activated fatty acids through the inner mitochondrial membrane into the mitochondrial matrix, where the $\beta$-oxidation of the fatty acids takes place. Shorter-chain fatty acids can freely pass the inner mitochondrial membrane. A deficiency of carnitine therefore has an adverse influence on the oxidation of long-chain fatty acids. Carnitine deficiency phenomena are treated by substitution therapy with L-carnitine. Since the necessary amounts of L-carnitine has not always been available, the racemic DL-carnitine has often been administered. DL-carnitine has been used in Europe as appetite stimulant, as additive for sports food and for treating cardiac diseases and obesity. Recently, however, there has been a tendency to administer only L-carnitine since it was determined that D-carnitine is a competitive inhibitor of carnitine-bound enzymes and can consequently cause undesired side effects.

Since the discovery of L-carnitine in muscle, L-carnitine has been obtained by expensive isolation and purification methods from animal tissue. In the fifties, multistage chemical syntheses were developed. However, these methods produce DL-carnitine. In order to isolate the L- isomer, it has been necessary to use methods based on racemate splitting by means of fractional crystallization, using optically active acids. Numerous biochemical methods for producing L-carnitine have also been described: For example, the hydroxylation of $\gamma$-butyrobetaine, the reduction of 3-dehydrocarnitine, the conversion of crotonobetaine, the hydrolysis of DL-carnitine nitrile. All these methods have disadvantages from the standpoint of industrial application, since either the initial materials are expensive, the enzymes used are unstable or have insufficient stereoselectivity or activity or the use of expensive coenzymes is necessary.

SUMMARY OF THE INVENTION

The present invention provides the microorganism having the deposit number DSM 6230. It also provides a microbiologically produced L-carnitine amidase which is characterized by the following properties:

a) Reactivity

It hydrolyzes L-carnitine amide to L-carnitine and ammonia, b) Substrate specificity

It does not hydrolyze D-carnitine amide, any aliphatic or aromatic carboxylic acid amides, any amino acid amides or any dipeptide amides.

c) Inductor

It is an inducible enzyme and is induced by L-carnitine amide, L-carnitine, $\gamma$-butyrobetaine and dehydrocarnitine.

d) Optimum pH

The optimum pH range is between pH 7.0 and pH 9.5.

e) pH stability

It has good pH stability in the pH range between pH 5.0 and pH 9.5.

f) Inhibitors $Zn^{2+}$, $Cu^{2+}$, $Hg^{2+}$ and $Ag^{2+}$, as well as p-hydroxymercuribenzoate, phenylmethane sulfonyl fluoride and dinitrodithiobenzoic acid exhibit an inhibiting action at a concentration of 1 mM or more.

g) Molecular weight

The molecular weight is approximately 130,000.

h) Subunits

It consists of two identical subunits with a molecular weight of approximately 65,000 each.

i) Isoelectric point

The isoelectric point is approximately pH 4.2.

j) Amino acid sequence (Seq. ID. No. 1)

The first 48 N-terminal amino acids are:

| | |
|---|---|
| Gly—Ser—Arg—Glu—Ile—Leu—Asp—Phe—Lys—Asp— | 10 |
| Leu—Ser—Ser—Pro—Ser—Ala—Pro—Ala—Glu—Leu— | 20 |
| Val—Ala—Asn—Ala—Ala—Phe—Leu—Glu—Pro—Ala— | 30 |
| Gly—His—Ala—Ala—Ala—His—Glu—Pro—Phe—Asn— | 40 |
| Gly—Gln—Ile—Thr—Leu—Gly—Glu—Thr— | 48 |

The invention also provides a method of obtaining the above-described L-carnitine amidase. In this method, the strain DSM 6230 is aerobically cultivated in an aqueous substrate containing mineral salts, one of the above-named inductors and a source for carbon and nitrogen at a temperature of 20° C. to 30° C. and an initial pH between 6.5 and 8.5. The cell mass is separated and the enzyme is isolated from the cells.

Finally, the invention provides a method of using the microorganism DSM 6230 or the L-carnitine amidase obtainable from it for the enzymatic conversion of L and/or DL-carnitine amide to L-carnitine.

Microorganism strain DSM 6230 was deposited on Oct. 1, 1990 in the Deutsche Sammlung von Mikroorganismen und Zellkulturen GmbH [German Collection of Microorganisms and Cell Cultures Ltd.]. It grows in rods with a length of 1.5 to 2.5 μm and a width of 0.5 to 0.7 μm, exhibits no Gram reaction, lysis is effected by 3% KOH or amino peptidase (Cerny). The strain forms no spores and contains an oxidase and a catalase. It does not grow anaerobically, grows aerobically at 37° C., but not at 41° C. and not at a pH of 5.6; it grows on MacConkey's agar but not on SS agar or cetrimide agar. It contains no diffusing or diffusing and fluorescing pigments and no pyocyanin. It does not form acids either aerobically or anaerobically from glucose in an OF test and develops no gas from glucose. In the ASS test, it forms acids from glucose and xylose but not from fructose. It forms no ADH, ODC, LDC, ONPG, VP and no indol. It does not reduce $NO_3$ to $NO_2$ and effects no denitrification. It forms a phenylalanine desaminase, no levan from saccharose, no lecithinase and no urease.

It does not hydrolyze starch, gelatin, casein, DNA, Tween 80 or aesculin and does not degrade tyrosine. It utilizes acetate, malate, phenyl acetate and fructose as substrate but not adipate, citrate, glycolate, lactate, laevulinate, malonate, suberate, L-arabinose, glucose, mannose, maltose, xylose, mannitol, gluconate, 2-ketogluconate, N-acetyl glucosamine, L-serine, L-histidine and hydroxybutyrate. The main quinone component is ubiquinone 10.

The microorganism strain DSM 6230 can not be unambiguously associated with any previously described species. However, based on its cellular fatty-acid pattern and the quinone components, this bacterium should be associated with the α subgroup of the purple bacteria and is thus close, for example, to the Agrobacterium and Sphingomonas genera. An unambiguous delimitation from the authentic strains of the Pseudomonas genus can determined, base don the quinone composition and on the cellular fatty acids.

The most important morphological, physiological and biochemical qualities are collated in the following table.

| | | | |
|---|---|---|---|
| Cell form | rod | $NO_2$ from $NO_3$ | − |
| Width μm | 0.5–0.7 | | |
| Length μm | 1.5–2.5 | Denitrification | − |
| Gram reaction | − | Phenylalanine desaminase | + |
| Lysis by 3% KOH | + | | |
| Aminopeptidase (Cerny) | + | Levan from saccharose | − |
| Spores | − | Lecithinase | − |
| Oxidase | + | Urease | − |
| Catalase | + | Hydrolysis of starch | − |
| Growth | − | Gelatin | − |
| anaerobic | | Casein | − |
| 37/41° C. | +/− | DNA | − |
| pH 5.6 | − | Tween 80 | − |
| Mac-Conkey's agar | + | Aesculin | − |
| SS agar | − | | |
| Cetrimide agar | − | Tyrosine degradation | − |
| Pigments | − | Substrate evaluation | |
| Non-diffusing | − | Acetate | + |
| Diffusing | − | Adipate | − |
| Fluorescing | − | Citrate | − |
| Pyocyanin | − | Glycolate | − |
| | | Lactate | − |
| Acid from (OF test) | | Levulinate | − |
| Glucose aerobic | − | Malate | + |
| Glucose anaerobic | − | Malonate | − |
| | | Phenyl acetate | + |
| Gas from glucose | − | Suberate | − |
| | | L-arabinose | − |
| Acid from (ASS) | | Fructose | + |
| Glucose | + | Glucose | − |
| Fructose | − | Mannose | − |
| Xylose | + | Maltose | − |
| | | Xylose | − |
| ADH | − | Mannitol | − |
| | | Gluconate | − |
| ODC | − | 2-ketogluconate | − |
| | | N-acetyl glucose amine | − |
| LDC | − | L-serine | − |
| | | L-histidine | − |
| ONPG | − | Hydroxybutyrate | − |
| VP | − | Main quinone component: ubiquinone 10 | |
| Indol | − | | |

The present invention provides a method for obtaining of L-carnitine from DL- and/or L-carnitine amide. DL-carnitine amide is a stable compound which can be produced relatively economically, starting with epichlorohydrin.

The hydrolysis of DL- and/or L-carnitine amide by means of L-carnitine amide hydrolases is described in published German Patent Application DOS 37 28 321 (U.S. Pat. No. 4,918,012). The enzymes are produced by pseudomonads which have not been given any species name. All these pseudomonads have 2 carnitine amide hydrolases, an L-specific enzyme whose substrate is L-carnitine and a D-specific enzyme which converts L-carnitine amide. The effectiveness of both enzymes can vary considerably, depending on the strain and the conditions of growth. Only the L-carnitine amide hydrolase is described in detail.

The following table is intended to contrast the properties of this L-carnitine amide hydrolase with those of the L-carnitine amidase in accordance with the present invention.

| | L-carnitine amide hydrolase | | L-carnitine amidase | |
|---|---|---|---|---|
| Inducibility [ability to be induced] | + | | + | |
| Inductors: | | | | |
| Carnitine | + | | + | |
| Carnitine amide | + | | + | |
| γ-butyrobetaine | + | | + | |
| Substrate spectrum: | | | | |
| D-carnitine amide | − | | − | |
| Acetamide | − | | − | |
| Butyramide | − | | − | |
| Benzamide | − | | − | |
| Inhibitors: | (1 mM) | (10 mM) | (1 mM) | (10 mM) |
| $Ag^{2+}$ | + | + | + | n.b. |
| $Cu^{2+}$ | − | k.A. | + | + |
| $Mn^{2+}$ | − | k.A. | + | + |
| $Mg^{2+}$ | − | k.A. | + | + |
| $Zn^{2+}$ | − | k.A. | + | n.b. |
| $Co^{2+}$ | − | k.A. | + | + |
| $Fe^{2+}$ | − | + | + | + |
| 2-mercaptoethanol | − | − | − | − |
| EDTA | − | − | + | + |
| Optimum pH: | pH 6–pH 7 | | pH 7–pH 9.5 | |
| Stable pH range | pH 5–pH 8 | | pH 5–pH 9.5 | |
| Molecular weight: | ca. 36,000 | | ca. 130,000 | |
| Subunits: | k.A. | | 2 | | k.A. = no data
n.b. = not determined

Both enzymes exhibit similarities with respect to inducibility, inductors, substrate spectrum, inhibition by silver ions (1 mM) and ferro ions (10 mM) and the lack of inhibition by 2-mercaptoethanol. There is no similarity in the case of the other properties cited. It becomes clear, especially when the molecular weights are compared, that the previously-described L-carnitine amide hydrolase and the L-carnitine amidase of the present invention are two completely different enzymes.

DETAILED DESCRIPTION OF PREFERRED EMBODIMENTS

The invention is illustrated in more detail in the following examples:

EXAMPLE 1

Search for carnitine amidases

Soil, water and sewage plant specimens from a total of 267 sites were examined in a comprehensive screening. The work was performed with direct plating and enriched cultures, with full and with minimum media, with minimum media and additional carbon sources and with various acid amides as inductors and/or carbon sources and/or nitrogen sources. To this end, the specimens were suspended or diluted with a 0.9% solution of sodium chloride and agitated for 4-6 hours for a thorough mixing or rinsing. Aliquots of the supernatants were either plated out after a suitable dilution onto plates with solid media or placed into 100 ml Erlenmeyer flasks containing 20 ml liquid medium. The plates were incubated for 3-7 days in an incubator before individual colonies were isolated from them and brought into pure culture.

The liquid cultures were incubated in a rotary agitator at 30° C. and 120 rpms for 3-7 days. After this time, aliquots were taken from the culture liquids and new 20 ml liquid cultures were inoculated with them which cultures were incubated under the same conditions. This process was repeated approximately five times before specimens of the culture liquids were plated out after a suitable dilution onto plates with a solid medium. The plates were incubated 3-7 days at 30° C. in an incubator before individual cultures were isolated from them and brought into pure culture.

| Media composition: | |
| --- | --- |
| Minimum medium: | |
| K$_2$HPO$_4$ | 2.50 g |
| KH$_2$PO$_4$ | 1.95 g |
| NaCl | 1.00 g |
| CaCl$_2$ × 2H$_2$O | 0.05 g |
| MgSO$_4$ × 7H$_2$O | 0.30 g |
| yeast extract | 0.50 g |
| DL-carnitine amide | 5.00 g |
| trace salt solution | 0.80 ml |
| diluted with distilled water to pH 7.2 | 1.0 l |
| plates with 1.8% agar | |
| Trace salts solution: | |
| H$_3$BO$_3$ | 75.0 mg |
| MnCl$_2$ × 4H$_2$O | 50.0 mg |
| ZnCl$_2$ | 187.5 mg |
| CuSO$_4$ × 5H$_2$O | 50.0 mg |
| FeCl$_3$ × 6H$_2$O | 625.0 mg |
| (NH$_4$)$_8$Mo$_7$O$_{24}$ × H$_2$O | 25.0 mg |
| CoSO$_4$ × 7H$_2$O | 37.5 mg |
| diluted with distilled water to | 0.2 l |
| Minimum medium + additional carbon sources: | |
| minimum medium + | 2.50 ml |
| glycerol | |
| and/or malic acid | 2.50 g |
| Minimum medium + additional acid amides: | |
| minimum medium with 2.5 g | 2.50 g |
| DL-carnitine amide + acetamide or propionamide | |
| Full medium: | |
| minimum medium + | 0.50 g |
| casein | |
| peptone | 0.50 g |
| meat extract | 0.50 g |
| malt extract | 0.50 g |
| glycerol | 0.50 g |

CaCl$_2$, MgSO$_4$, DL-carnitine amide, acetamide and propionamide were added to the culture liquids after the autoclaving under sterile conditions.

1367 strains were isolated during the screening program. These strains were incubated in 100 ml Erlenmeyer flasks containing 20 ml of the particular enrichment medium in a rotary agitator at 30° C. and 120 rpms. The optical density at 660 nm was taken as an indication for the cell growth.

After 3 days, the contents of the shaking flasks were centrifuged (10 min., 10000 rpms in a refrigerated centrifuge), and the sedimentated cells were taken up in 100 mM potassium phosphate buffer pH 7.5 (an approximately 20% microorganism suspension was produced).

The microorganisms in this suspension must be macerated in the customary manner (e.g. agitation with fine glass beads or ultrasound treatment). The cell maceration was carried out by means of wet grinding with glass beads (diameter 0.3 mm; 2 g beads per 1 ml cell suspension). The glass beads and the coarse cell fragments were centrifuged off by means of centrifugation in a refrigerated centrifuge (5 min. 12000 rpms). The clear supernatant was designated as raw extract and used for further experiments.

The determination of the protein concentration was carried out according to the method of Bradford.

Carnitine and ammonia are formed in the same molar ratio in the conversion of carnitine amide to carnitine.

carnitine amide + H$_2$O $\xrightarrow{\text{carnitine amidase}}$ carnitine + NH$_3$ Therefore, arrangements for the determination of enzyme activities are:
measuring the decrease of the carnitine amide,
measuring the carnitine formed
measuring the ammonia formed.

The materials for the activity test contained:
400 μl potassium phosphate buffer 0.1 M, pH 7.5
50 μl substrate in 0.1 M potassium phosphate buffer, pH 7.5
50 μl enzyme solution (raw extract)

The following were used as substrates:
a) DL-carnitine amide final concentration in the test 100 mM
b) D-carnitine amide final concentration in the test 50 mM c) L-carnitine amide final concentration in the test 50 mM The enzyme test was carried out in 1.5 ml Eppendorf vessels at a temperature of 30° C. The reaction was started by the addition of enzyme solution and stopped by acidification. The precipitated protein was centrifuged off (Eppendorf centrifuge 5 min. 12500 rpms) and the supernatant examined. In order to determine the blank reading, a control specimen for the substrate and the enzyme solution was always used.

The definition of the enzyme unit is 1 mU=1 nM converted substrate per minute.

The determination of carnitine and carnitine amide can be carried out with thin-layer chromatography. Silica gel plates of the Merck company were used as adsorbent, onto each of which plates 3 μl of the liquids to be examined were applied. Carnitine and carnitine amide were detected with iodine vapor.

The composition of the mobile solvents and the R$_F$ values are given in the following table.

| Mobile solvent | Substance | R$_F$ value |
| --- | --- | --- |
| Chloroform/methanol/water/ | carnitine | 0.44 |
| formic acid conc./ammonia conc. | carnitine amide | 0.51 |

-continued

| 50/55/10/5/7.5 Chloroform/methanol/water formic acid conc. 50/50/17.25/0.425 | carnitine carnitine amide | 0.35 0.45 |
|---|---|---|

| Carnitine and carnitine amide can be determined with the HPLC system: | |
|---|---|
| Stationary phase: | NH₃ |
| Column - column number: | BK 3/88 |
| Column diameter inner: | 5 mm |
| Temperature: | 45° C. |
| Mobile phase A: | 670 ml acetonitrile f. chr. |
| Mobile phase B: | 330 ml 0.05 M (NH$_4$)$_2$ HPO$_4$ |
| Rate of flow: | 0.7 ml/min. |
| Wavelength: | 205 mn |
| Injection volume | 20 μl |

L-carnitine can be determined enzymatically with the carnitine acetyl transferase. The ammonia was determined on the one hand photometrically as indophenol and on the other hand enzymatically with the aid of glutamate dehydrogenase.

Of the 1367 strains isolated, 65 exhibit amidase activity. The enzyme activities extend from a few mU to several U. One strain was selected from the active strains in order to allow it to be determined in the Deutsche Sammlung von Mikroorganismen und Zellkulturen [German Collection of Microorganisms and Cell Cultures] (DSM).

The raw extract of this strain was tested with enantiomerically pure D- and L-carnitine amide:

| Activity D-amide | (mU/ml) L-amide | Activity D-amide | (mU/mg) L-amide | L-amidase activity (%) |
|---|---|---|---|---|
| 0 | 8624 | 0 | 1960 | 100 |

EXAMPLE 2

Closer examination of the amidase activity

The raw extract was retested for D- and L-carnitine amide and the enzyme test was stopped after 10 min. (there is still sufficient L-carnitine amide in the test batch) and after 5 hours (the L-carnitine amide has reacted to a great extent or completely). The L-amidase activity, relative to the total amidase activity, was 100% after 10 min. and still over 99% after 5 hours. This test shows that the raw extract of strain DSM 6230 forms hardly any measurable D-carnitine even after an incubation period of 5 hours. This strain accordingly exhibits a very high selectivity of the amidase reaction in addition to a high enzyme activity.

EXAMPLE 3

Test for the induction of L-carnitine amidase

In this test, various substances were examined for their induction action. At the same time, the growth on these compounds was followed. The medium used was a minimum medium with 1.0 g/l instead of 0.5 g/l yeast extract, to which 5 g/l of the substance to be tested were added in each instance. The culture without inductor contained 5 g/l yeast extract. All tests were carried out with 20 ml shaking cultures which were incubated 36 h at 30° C. and 120 rpms in a rotating [round]shaking machine. These cultures were inoculated with 1% of an initial culture of strain DSM 6230. L-carnitine amide was used as substrate for the enzyme test.

The results of this test are given in the following table:

| Inductor | $OD_{660}$ | Activity (mU/ml) | Activity (mU/mg) | mU/mg (%) |
|---|---|---|---|---|
| L-carnitine amide | 3.5 | 8530 | 1706 | 100 |
| Without | 2.8 | 129 | 39 | 2 |
| D-carnitine amide | 0.8 | 497 | 166 | 10 |
| DL-carnitine amide | 2.7 | 8867 | 1673 | 98 |
| DL-carnitine | 2.5 | 5773 | 1255 | 74 |
| γ-butyrobetaine | 0.7 | 963 | 566 | 33 |
| Dehydrocarnitine | 0.8 | 837 | 279 | 16 |
| Glycine betaine | 2.9 | 183 | 33 | 2 |
| D-carnitine nitrile | 0.8 | 206 | 90 | 5 |
| L-carnitine nitrile | 0.8 | 183 | 65 | 4 |
| DL-carnitine nitrile | 0.8 | 221 | 88 | 5 |
| D-leucine amide | 0.8 | 170 | 81 | 5 |
| L-leucine amide | 2.5 | 34 | 9 | <1 |
| L-proline amide | 1.0 | 250 | 54 | 3 |
| L-phenylalanine amide | 0.6 | 172 | 72 | 4 |
| L-valine amide | 0.9 | 32 | 12 | <1 |
| Glycine amide | 1.0 | 180 | 43 | 3 |
| Acetamide | 1.0 | 0 | 0 | 0 |
| Propionamide | 1.1 | 129 | 29 | 2 |
| Butyramide | 0.9 | 54 | 18 | 1 |
| Isobutyramide | 1.1 | 193 | 41 | 2 |
| Lactic acid amide | 0.8 | 55 | 28 | 2 |
| Acrylamide | 0.8 | 170 | 136 | 8 |
| Methacrylamide | 0.8 | 237 | 76 | 4 |
| Benzamide | 0.3 | 0 | 0 | 0 |
| Nicotinamide | 0.7 | 55 | 28 | 2 |

The test clearly shows that L-carnitine amidase is an inducible enzyme. Inductors are: L-carnitine amide, L-carnitine, γ-butyrobetaine and dehydrocarnitine. The best of the inductors tested is L-carnitine amide.

Good growth is shown by the strain on L-leucinamide, L-carnitine amide, DL-carnitine amide, DL-carnitine and glycine betaine. L-leucinamide and glycine amide are merely good growth substrates, the L-carnitine amidase is not induced by them. On the other hand, γ-butyrobetaine and dehydrocarnitine induce the enzyme but can not be metabolized or are metabolized very poorly.

EXAMPLE 4

Determination of the optimum inductor concentration

The induction of L-carnitine amidase at various concentrations of DL-carnitine amide in the culture medium was examined in a further test. At the same time, the growth of the bacteria was followed in these carnitine amide concentrations. The culture conditions corresponded to those in example 3.

The results of this test are shown in the following table:

| carnitine amide concentration (g/l) | $OD_{660}$ nm | amidase activity (U/ml) |
|---|---|---|
| 0.5 | 1.1 | 0.7 |
| 1.0 | 1.3 | 2.4 |
| 2.0 | 1.7 | 6.1 |
| 3.0 | 2.0 | 7.3 |
| 5.0 | 2.8 | 8.9 |
| 7.5 | 4.0 | 10.6 |
| 10.0 | 3.9 | 8.6 |
| 15.0 | 3.7 | 7.3 |
| 20.0 | 3.6 | 7.1 |
| 25.0 | 3.5 | 6.7 |

This test shows that the optimum DL-carnitine amide concentration, both for the growth of the bacteria as well as for the amidase activity under the culture conditions cited above, is 7.5 g/l.

EXAMPLE 5

L-carnitine amidase fermentation on an 8 liter scale

A bioreactor equipped as follows was used:
Agitator mechanism
Speed control
Temperature control circuit with thermosensor
Sterile filter for air supply and removal
pH electrode
Antifoam probe
Acid, lye and antifoam storage vessels
Oxygen electrode The working volume was 8 liters, the pH of the fermentation medium 7.2 and the fermentation temperature 30° C. The medium was a minimum medium (see Example 1) with 1 g/l yeast extract and 7.5 g/l DL-carnitine amide. After the sterilization, the fermenter was inoculated with 200 ml of an starting culture of strain DSM 6230 which had been incubated for 24 hours at 120 rpms and 30° C. in a rotary shaker.

The fermentation was over after 17 hours. The $OD_{660}$ of the culture liquid was 3.2 at this time. 63 g moist cells were able to be harvested. A 20% cell suspension was produced with 100 mM potassium phosphate buffer pH 7.5 (final volume 315 ml). The cells were macerated by means of wet grinding with glass beads (diameter 0.3 mm). The volumetric activity per ml raw extract was 9590 mU and the specific activity 1314 mU. Thus, it was possible to obtain 3021 units of L-carnitine amidase from 8 liters of fermentation medium. No D-carnitine amidase activity was detectable in the raw extract.

EXAMPLE 6

Purification of L-carnitine amidase

It was possible to purify the L-carnitine amidase to total purity from the raw extract after precipitation of the nucleic acids with polyethylene imine (0.2%) via two ion exchangers ("Fractogel EMDTMAE-650 (S)" of the Merck company and "Mono-Q" of the Pharmacia company. The specific activities in the raw extract were 1.31 U per mg protein and 328 U per mg Mono-Q-purified enzyme. The enrichment factor for the enzyme was therefore 250.

EXAMPLE 7

Determination of the isoelectric point

The determination of the isoelectric point of L-carnitine amidase was carried out according to the Pharmacia Phast system method 100.

It was approximately pH 4.2.

EXAMPLE 8

Determination of the molecular weight and of the number of subunits

The molecular weight of the native enzyme was determined by means of gel filtration on Sephacryl S-200 HR. The column (1.6×69.6 cm) coupled to an FPLC system was operated with a flowthrough rate of 1 ml/min. The following served as reference proteins: Cytochrome C, myoglobin (whale), myoglobin (horse), carboxyanhydrase B, ovalbumin, BSA, R-oxinirilase (panic), aldolase (monomer) and aldolase (dimer) (rabbit muscle). The molecular weight of L-carnitine amidase is 125000±5000. A molecular weight of 65700 was determined for the denatured enzyme in gel electrophoresis in the presence of sodium dodecylsulfate (SDS). The amidase accordingly consists of two identical subunits. Reference proteins used were: $\alpha_2$-macroglobulin (horse) non-reduced and reduced, phosphorylase b (rabbit muscle), DSA, glutamate dehydrogenase (bovine liver), lactate dehydrogenase (swine liver) and the trypsin inhibitor from the soybean.

EXAMPLE 9 pH dependency of L-carnitine a) Dependency of the reaction speed on the pH

In order to determine the optimum pH, the enzyme test was carried out at various pH'es. The following buffers were used thereby: Citrate with pH 3–pH 6.5, potassium phosphate with pH 6.5–pH 8.5, tris/HCl with pH 8.5–pH 9.5 and bicarbonate with pH 9.5–pH 11. The substrate was adjusted in advance to the corresponding pH.

Enzyme activity is present from pH 4.5–pH 11. Good conversions are achieved in the range of pH 7–pH 9.5 The highest reaction speed is achieved at pH 8.5 in tris/HCl buffer.

b) Influence of the pH on the enzyme stability

In order to determine the enzyme stability as a function of the pH, enzyme solution was diluted tenfold with various buffers with different pH'es (see a) and incubated at 30° C. for 30 min. Then, these batches were centrifuged for 5 min. at 13000 rpms, after having cooled (2 min. on ice). 50 μl of these supernatants were used in each instance as enzyme solution in a conventional enzyme test, which was carried out in this case, however, in 200 mM potassium phosphate buffer. The enzyme exhibited good stability in a range from pH 5.0 to pH 9.5 The best stability is achieved between pH 7.5 and pH 8.5.

EXAMPLE 10

Influence of additives on the L-carnitine amidase activity

In order to test the influence of various additives on the enzyme activity, they were added to the test batches without substrate in a final concentration of 1 mM and 10 mM in each instance. The reaction batches were first incubated for 45 min. at 30° C. before the reaction was started by adding substrate solution.

The following table shows the results of these tests:

| Additive | Enzyme activity (%) | |
|---|---|---|
| | 1 mM | 10 mM |
| None | 100 | |
| bi- and trivalent cations: | | |
| $MgCl_2$ | 96 | 88 |
| $CaCl_2$ | 103 | 90 |
| $BaCl_2$ | 102 | 105 |
| $MnCl_2$ | 89 | 76 |
| $ZnCl_2$ | 6 | n.d. |
| $FeCl_2$ | 86 | 57 |
| $FeCl_3$ | 87 | 46 |
| $CoCl_2$ | 90 | 76 |
| $NiCl_2$ | 80 | 79 |
| $CuCl_2$ | 70 | 54 |
| Complexing agents: | | |
| Titriplex III (EDTA) | 93 | 73 |
| Phenanthroline | 89 | 82 |

-continued

| Additive | Enzyme activity (%) | |
|---|---|---|
| | 1 mM | 10 mM |
| Diethyl malonic acid | 92 | 68 |
| NaN$_3$ | 85 | 82 |
| Reducing agents: | | |
| 2-mercaptoethanol | 100 | 101 |
| Red. glutathione | 97 | 92 |
| Ethyl maleinimide | 100 | 99 |
| Dithiothreitol (DTT) | 94 | 101 |
| Dithioerythrite (DTE) | 98 | 99 |
| SH group reagents: | | |
| Para-hydroxymercuribenzoate (pOHMB) | 51 | n.d. |
| Iodoacetate | 97 | 72 |
| HnCl$_2$ | <1 | n.d. |
| AgNO$_3$ | 65 | n.d. |
| KCN | 85 | 88 |
| Inhibitors of PLP enzymes: | | |
| Cycloserine | 96 | 97 |
| Inhibitors of proteases: | | |
| Neostigmine bromide | 100 | 94 |
| Para-amino benzamidine hydrochloride (pABA) | 88 | 99 |
| Phenylmethane sulfonylfluoride (PMSF) | 23 | 2 |
| Na-tosyl-L-lysyl-chloromethane hydrochloride (TLCK) | 84 | 73 |
| Dinitrodithiodibenzoic acid | 34 | n.d. |
| α-ketoisocaproic acid | 92 | 90 |
| NaF | 88 | 78 |
| Acetaldehyde | 83 | 81 | n.d. = not determined

The bivalent metal ions $Zn^{2+}$ and $Cu^{2+}$, the SH group reagents $Hg^{2+}$, $Ag^{2+}$ and p-hydroxymercuribenzoate, and also the protease inhibitors phenylmethane sulfonylfluoride and dinitrodithiodibenzoic acid show a distinctly inhibiting action at a concentration as low as 1 mM. At a concentration of 10 mM, $Mn^{2+}$, $Fe^{2+}$, $Fe^{3+}$, $Co^{2+}$, EDTA, diethyl malonic acid, red. glutathione, iodoacetate, TLCK and NaF caused a reduction of the enzyme activity.

EXAMPLE 11

Substrate spectrum of L-carnitine amidase

The enzyme test was carried out at 30° C. in 100 mM potassium phosphate buffer pH 8. The substrate concentration was 50 mM.

The results of this test are shown in the following table:

| Substrate | Rel. activity (%) | Substrate | Rel. activity (%) |
|---|---|---|---|
| L-carnitine amide | 100 | Amino acid amides: | 0 |
| D-carnitine amide | 0 | L-Pro-NH$_2$ | 0 |
| D-carnitine nitrile | 0 | L-Ser-NH$_2$ | 0 |
| L-carnitine nitrile | 0 | 1-Thr-NH$_2$ | 0 |
| Acetamide | 0 | D-Phe-NH$_2$ | 0 |
| Propionamide | 0 | L-Phe-NH$_2$ | 0 |
| Butyramide | 0 | L-Tyr-NH$_2$ | 0 |
| Isobutyramide | 0 | L-Trp-NH$_2$ | 0 |
| Lactic acid amide | 0 | L-Arg-NH$_2$ | 0 |
| Acrylamide | 0 | L-His-NH$_2$ | 0 |
| Methacrylamide | 0 | L-Asn-NH$_2$ | 0 |
| Benzamide | 0 | L-Met-NH$_2$ | 0 |
| Amino acid amides: | | Dipeptide amides: | |
| Gly-NH$_2$ | 0 | L-Val-L-Phe-NH$_2$ | 0 |
| L-Val-NH$_2$ | 0 | L-Asp-L-Phe-NH$_2$ | 0 |
| Leu-NH$_2$ | 0 | L-Asp-L-Phe-NH$_2$ | 0 |
| L-Leu-NH$_2$ | 0 | L-Tyr-Gly-NH$_2$ | 0 |
| L-Ile-NH$_2$ | 0 | Gly-Gly-NH$_2$ | 0 |
| L-Ala-NH$_2$ | 0 | | |

The L-carnitine amidase is characterized by a very high substrate specificity. Aside from L-carnitine amide, none of the amides tested were converted. Thin-layer chromatographic tests showed that the amidase also has no proteolytic activity on the tested dipeptides.

EXAMPLE 12

Amino acid sequence of L-carnitine amidase

The amino acid sequence of the first 48 N-terminal amino acids was determined on a protein sequencator. For this, Mono-Q-purified enzyme concentrated by ultrafiltration dissolved in 10 mM potassium phosphate buffer pH 7.5was . charged. The amino acid sequence reads as follows (SEQ. ID. No: 1).

| | |
|---|---|
| Gly-Ser-Arg-Glu-Ile-Leu-Asp-Phe-Lys-Asp- | 10 |
| Leu-Ser-Ser-Pro-Ser-Ala-Pro-Ala-Glu-Leu- | 20 |
| Val-Ala-Asn-Ala-Ala-Phe-Leu-Glu-Pro-Ala- | 30 |
| Gly-His-Ala-Ala-Ala-His-Glu-Pro-Phe-Asn- | 40 |
| Gly-Gln-Ile-Thr-Leu-Gly-Glu-Thr- | 48 |

EXAMPLE 13

Conversion with whole cells

The conversion with whole cells was examined by carrying out the customary enzyme test with a 20% cell suspension of the strain DSM 6230. Result: L-carnitine amide is converted by whole cells with 64% greater activity than by a macerated cell suspension of the same concentration. D-carnitine is not converted. It is therefore to be expected that the conversion of L-carnitine amide to L-carnitine can also be carried out very well by means of immobilized microorganisms. The immobilization of the microorganisms by means of embedding into a polymer which does not denature the microorganisms can be carried out by methods known to persons skilled in the art. Suitable microorganism immobilizates are immobilizates based on alginate or chitosan.

What is claimed is:

1. Microbiologically produced L-carnitine amidase having the following properties:
a) Reactivity:
  It hydrolyzes L-carnitine amide to L-carnitine and ammonia,
b) Substrate specificity:
  It does not hydrolyze D-carnitine amide, any aliphatic or aromatic carboxylic acid amides, any amino acid amides or any dipeptide amides;
c) Inductors:
  It is an inducible enzyme and is induced by L-carnitine amide, L-carnitine, γ-butyrobetaine and dehydrocarnitine,
d) Optimum pH:
  The optimum pH range is between pH 7.0 and pH 9.5,
e) pH stability:
  It exhibits a good pH stability in the pH range between pH 5.0 and pH 9.5,
f) Inhibitors:
  $Zn^{2+}$, $Cu^{2+}$, $Hg^{2+}$ and $Ag^{2+}$, furthermore p-hydroxymercuribenzoate, phenylmethane sulfonyl fluoride and dinitrodithiobenzoic acid exhibit an inhibiting action at a concentration of 1 mM,
g) Molecular weight:
  The molecular weight is approximately 130,000 KD.
h) Subunits:
  It consists of two identical subunits with a molecular weight of approximately 65,000KD each,
i) Isoelectric point:
  The isoelectric point is approximately pH 4.2,
j) Amino acid sequence;
  The first 48 N-terminal amino acids SEQ. ID. No: 1 are:

Gly—Ser—Arg—Glu—Ile—Leu—Asp—Phe—Lys—Asp— 10

Leu—Ser—Ser—Pro—Ser—Ala—Pro—Ala—Glu—Leu— 20

Val—Ala—Asn—Ala—Ala—Phe—Leu—Glu—Pro—Ala— 30

Gly—His—Ala—Ala—Ala—His—Glu—Pro—Phe—Asn— 40

Gly—Gln—Ile—Thr—Leu—Gly—Glu—Thr— 48

* * * * *